(12) United States Patent
Choi et al.

(10) Patent No.: US 11,524,088 B2
(45) Date of Patent: Dec. 13, 2022

(54) PORTABLE STERILIZER

(71) Applicant: PARTICLE CO.,LTD., Chungcheongnam-do (KR)

(72) Inventors: Doo Hyun Choi, Gyeonggi-do (KR); Dong Ju Lee, Chungcheongbuk-do (KR); Youn Goo Choi, Chungcheongnam-do (KR)

(73) Assignee: PARTICLE CO., LTD., Chungcheongnam-Do (KR)

( * ) Notice: Subject to any disclaimer, the term of this patent is extended or adjusted under 35 U.S.C. 154(b) by 0 days.

(21) Appl. No.: 17/641,498

(22) PCT Filed: Sep. 1, 2020

(86) PCT No.: PCT/KR2020/011708
§ 371 (c)(1),
(2) Date: Mar. 9, 2022

(87) PCT Pub. No.: WO2021/049804
PCT Pub. Date: Mar. 18, 2021

(65) Prior Publication Data
US 2022/0305162 A1    Sep. 29, 2022

(30) Foreign Application Priority Data

Sep. 9, 2019   (KR) .......................... 10-2019-0111224

(51) Int. Cl.
*A61L 9/00* (2006.01)
*A01M 13/00* (2006.01)
(Continued)

(52) U.S. Cl.
CPC .................. *A61L 2/22* (2013.01); *A61L 2/18* (2013.01); A61L 2202/15 (2013.01); A61L 2202/16 (2013.01)

(58) Field of Classification Search
CPC .......... A61L 9/00; A61L 9/14; A61L 2209/00; A61L 2209/135; A01M 7/00; B05B 1/30; B05B 17/06
(Continued)

(56) References Cited

U.S. PATENT DOCUMENTS

2010/0147701 A1\*  6/2010  Field ....................... A47L 13/22
204/230.2

FOREIGN PATENT DOCUMENTS

KR          10-1241051 B1      3/2013
KR          10-1400082 B1      5/2014
(Continued)

OTHER PUBLICATIONS

International Search Report for PCT/KR2020/011708 dated Mar. 22, 2021.

*Primary Examiner* — Monzer R Chorbaji
(74) *Attorney, Agent, or Firm* — The PL Law Group, PLLC (57) ABSTRACT

A portable sterilizer according to an embodiment of the present application is capable of spraying ultra-fine chemicals, and includes a housing in which a space is formed and an injection nozzle is provided at a front end thereof, a chemical tank provided on one side of the space of the housing, a chemical feed pipe formed between the chemical tank and the injection nozzle, and a water pump which is installed on one side of the chemical supply pipe to supply the chemical to the injection nozzle through the chemical supply pipe.

6 Claims, 5 Drawing Sheets

(51) Int. Cl.
*A01M 19/00* (2006.01)
*A01M 7/00* (2006.01)
*A61L 2/22* (2006.01)
*A61L 2/18* (2006.01)

(58) Field of Classification Search
USPC .............. 422/305–306; 43/125, 129, 900
See application file for complete search history.

(56) References Cited

FOREIGN PATENT DOCUMENTS

| | | | |
|---|---|---|---|
| KR | 10-1692347 B1 | 1/2017 | |
| KR | 10-1820506 B1 | 1/2018 | |
| WO | WO 2006/004609 A2 | 1/2006 | |
| WO | WO-2006004609 A2 * | 1/2006 | ........... B05B 7/0081 |

* cited by examiner

PORTABLE STERILIZER

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2020/011708, filed Sep. 1, 2020, which claims priority to the benefit of Korean Patent Application No. 10-2019-0111224 filed in the Korean Intellectual Property Office on Sep. 9, 2019, the entire contents of which are incorporated herein by reference.

BACKGROUND

1. Technical Field

The present invention relates to a sterilizer and, more particularly, to a portable sterilizer capable of spraying ultra-fine chemicals.

2. Description of the Related Art

In general, a quarantine device such as a fumigator is manufactured in a portable type and used for disinfection of factories, buildings, houses, etc., spray disinfection of cultivated fields such as fruit trees and vegetables, and disinfection of stables for livestock such as pigs, dairy farms, and poultry.

Workers may carry out prevention and quarantine work by mounting the quarantine device on a vehicle or cart, or by directly lifting or carrying the same.

Such a quarantine device is used in such a manner that fuel (gasoline, LPG, diesel, kerosene, etc.) is burnt to vaporize or evaporate a chemical liquid, and/or by a method for pressurized spraying.

A sprayer that applies pressure to a liquid and distributes the liquid over a large area may be classified in various ways depending on an operation method, use, size, and the like. In other words, since the size, shape and/or spray area of particles to be sprayed amorphously or granularly need to be varied according to the use of the particles such as household, agricultural, industrial, etc. and targets for spraying, different types of sprayers are required.

On the other hand, in the case of a nebulizer for disease prevention or sterilization, it is advantageous in terms of disease prevention effects to evenly distribute the chemical solution over a wider area, therefore, nebulizers with a particle size of several tens to several hundreds μm are preferred.

As described above, the nebulizer mainly used for disease prevention and disinfection is often called a chemical solution sprayer, a fumigator, a sterilizer, and the like.

However, the conventional nebulizer can pulverize a chemical solution to make it uniform and then spray the same over a large area in a short distance, but has a disadvantage of not spraying uniformly pulverized chemical solution far away.

Further, since the particles (30 μm to 50 μm) sprayed in the air spraying method from the conventional sprayer are large, the chemical solution may leave a trace on furniture such as desks or tables or electronic products such as computers, TVs, etc. after falling thereon.

Further, the conventional sprayer uses a built-in battery and, when the charged battery is discharged while conducting prevention and disinfection work, the main body itself should be charged to thus causing inconvenience and increase in working time.

SUMMARY

The present invention has been devised to solve the above problems, and an object of the present invention is to provide a portable sterilizer capable of spraying ultra-fine particles.

Another object of the present invention is to provide a portable sterilizer that is provided with a detachable battery and enables continuous sterilization only by replacing the battery when necessary.

In order to solve the above problems, the present invention provides a portable sterilizer, including: a housing in which a space is formed, and an injection nozzle is provided at a front end of the housing; a chemical tank provided on one side of the space in the housing; a chemical feed pipe formed between the chemical tank and the injection nozzle; and a water pump installed on one side of the chemical feed pipe to supply chemicals to the injection nozzle through the chemical feed pipe.

According to one feature of the present invention, a handle may be provided on the top of a rear end of the housing.

According to another feature of the present invention, a battery may be detachably coupled to the bottom of the rear end of the housing.

According to another feature of the present invention, the injection nozzle may include: a conical nozzle member formed to become narrower in width from the rear end to the front end thereof; a blower installed in the rear of the nozzle member and provided with a blower fan; and a connection part between the nozzle member and the blower fan, into which an end of the chemical feed pipe is inserted.

According to another feature of the present invention, a pair of mist nozzles may be coupled to the end of the chemical feed pipe.

According to another feature of the present invention, in order to return the chemicals remaining in the injection nozzle back to the chemical tank, a chemical recovery pipe extending from the connection part to the chemical tank may further be included.

According to another feature of the present invention, the nozzle member may further include: a conical body; a flange part extending from the rear end of the body; and a locking part extending in width along the periphery of the front end of the flange part.

According to the portable sterilizer of the present invention, a floating time of the sprayed ultra-fine particles in the air may be increased, thereby preventing secondary contamination and improving disinfection and disease prevention efficiencies.

Further, the portable sterilizer according to the present invention adopts a detachable battery, thereby continuously working with the battery additionally charged when discharged.

DETAILED DESCRIPTION

Hereinafter, embodiments of the present invention will be described in detail with reference to the accompanying drawings. However, the embodiments described below are merely for explaining in detail enough that one of ordinary skill in the art to which the present invention pertains can easily practice the invention, which does not mean that the protection scope of the present invention is limited. In describing various embodiments of the present invention, the same reference numerals will be used for components having the same technical characteristics.

Figure 1:
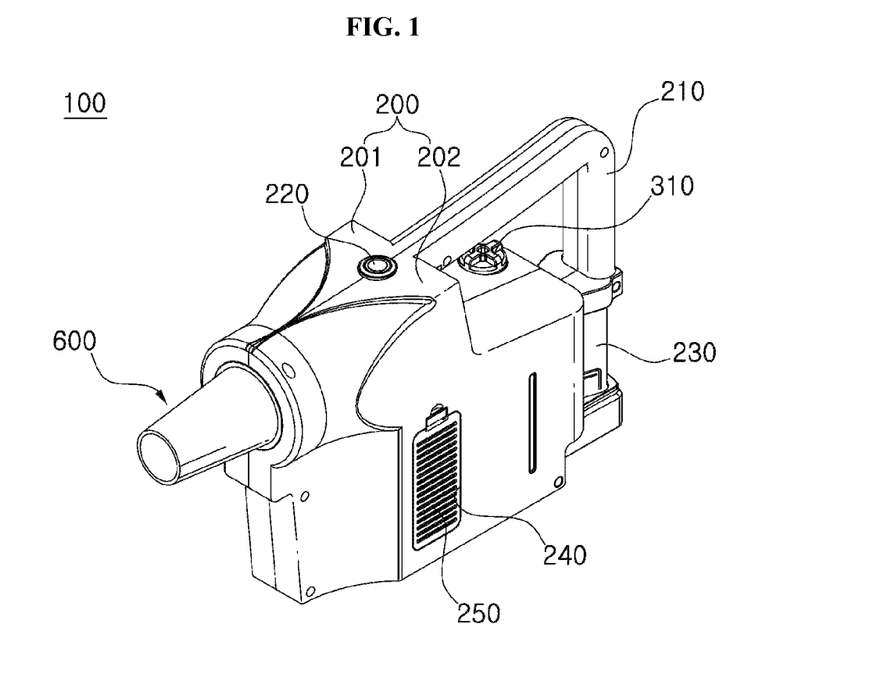
FIG. 1 is a perspective view of the portable sterilizer according to an embodiment of the present invention.
Figure 2:
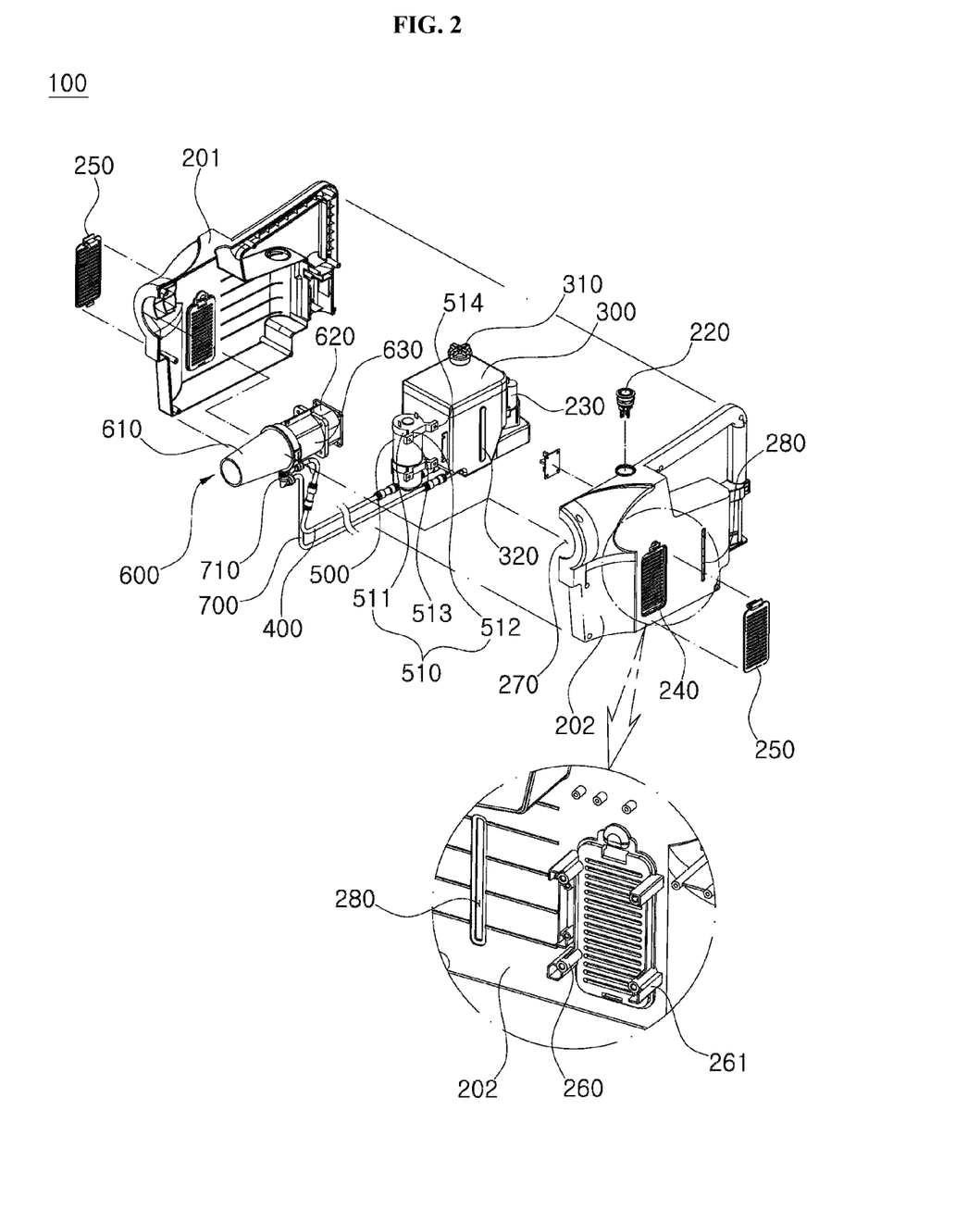
FIG. 2 is an exploded perspective view of the portable sterilizer according to an embodiment of the present invention.
Figure 3:
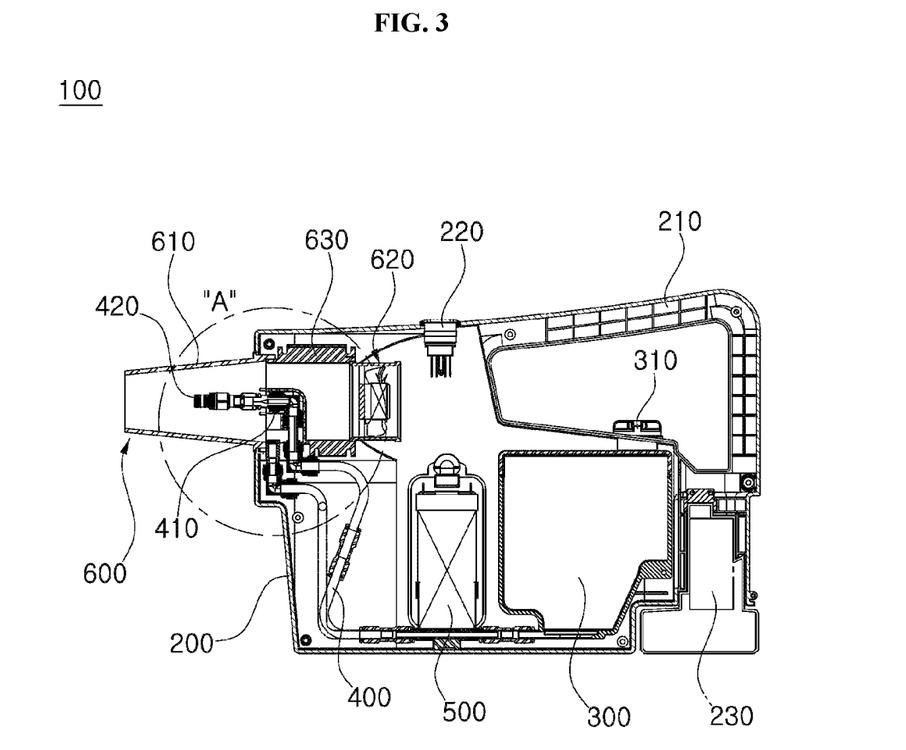
FIG. 3 is a cross-sectional view of the portable sterilizer according to an embodiment of the present invention.

As shown in FIGS. 1 to 3, the portable sterilizer 100 according to an embodiment of the present invention may include: a housing 200 provided with an injection nozzle at a front end thereof; a chemical tank 300 installed inside the housing 200; a chemical feed pipe 400; and a water pump 500.

A space may be formed inside the housing 200, in which the chemical tank 300, the chemical feed pipe 400 and the water pump 500 are disposed.

For example, the housing 200 may include a first housing 201 and a second housing 202 in left and right symmetrical shapes, wherein the chemical tank 300, the chemical feed pipe 400 and the water pump 500 are firstly mounted in a space of the first housing, followed by putting the second housing 202 thereon and coupling the same with the first housing 201. Further, a ventilation hole 240 may be perforated through one side of each of the first housing 201 and the second housing 202, and may be provided with a dust filter 250.

An external appearance of the housing 200 may be appropriately selected as needed, and a handle 210 may be provided on the rear end of the housing 200 to be portable. Further, a power button 220 for turning on/off operation of the portable sterilizer 100 may be provided on the top of the housing 200 in front of the handle 210.

In addition, a battery 230 may be coupled to a lower side of the rear end of the housing 200, that is, a lower side of the handle 210, and this battery 230 may be detachable from the housing 200 so that the user can separate the discharged battery 230 from the housing 200 and then connect a new charged battery 230 to the housing 200, thereby continuously proceeding sterilization and disinfection without requiring a separate charging time.

The chemical tank 300 may be installed on one side of the space of the housing 200. The chemical tank 300 may contain various kinds of prevention chemicals such as sterilizing disinfectant, insect repellent, phytoncide, etc. depending on situations. The chemical tank 300 may be provided with a lid 310 on the top of the tank in order to open/close the chemical tank 300, which is coupled to the tank, for example, in a screw joint manner. The lid 310 may be exposed to the outside of the housing 200 so that the user can open the lid 310 and then remove or supplement the chemicals in the chemical tank 300.

The chemical tank 300 may be provided with a flow meter 320 on a lateral side of the tank in order to visually check a level of the chemicals stored therein, and the flow meter 320 of the chemical tank 300 may be seen from the outside through a cut-out groove 280 of the housing 200.

The water pump 500 may be installed in front of the chemical tank 300. The water pump 550 may be mounted and fixed on one inner surface of the housing 200 by a fixing bracket 510. At this time, the fixing bracket 510 may include: a ring type body 511; a pair of support parts 512 being spaced from one side of the body 511 by a predetermined distance and extending therefrom; and a coupling part 513 bent outward and extending from an end of the support part 512. The pair of support parts 512 may obliquely extend such that a distance between each other increases toward the outside of the body 511, and a fastening hole 514 may be formed to perforate through the coupling part 513.

A plurality of coupling bosses 260 may be protruded from the inner surface of one side of the housing 200, and the fixing bracket 510 may be fixed to the inside of the housing 200 by a fastening member (not shown) such as bolts, screws, etc., which penetrate the fastening hole 514 of the coupling part 513 and fastened to the coupling bosses 260.

For example, a pair of fixing brackets 510 may be coupled to upper and lower ends of the water pump 500, respectively (one by one), wherein the body 511 of the fixing bracket 510 is combined to surround an outer circumference (or periphery) of the water pump 500. Further, on the outside of each coupling boss 260, a reinforcing member 261 having a "L"-shaped cross-sectional shape may be provided to support the coupling part 513 of the fixing bracket 510, and this reinforcing member 261 may be formed integrally with the boss 260.

On the other hand, the chemical feed pipe 400 extending from the lower end of the chemical tank 300 may extend to the injection nozzle 600 through the water pump 500. Therefore, when the power button 220 is turned ON to operate the water pump 500, the chemicals contained in the chemical tank 300 may be fed to the injection nozzle 600 through the chemical feed pipe 400.

Figure 4:
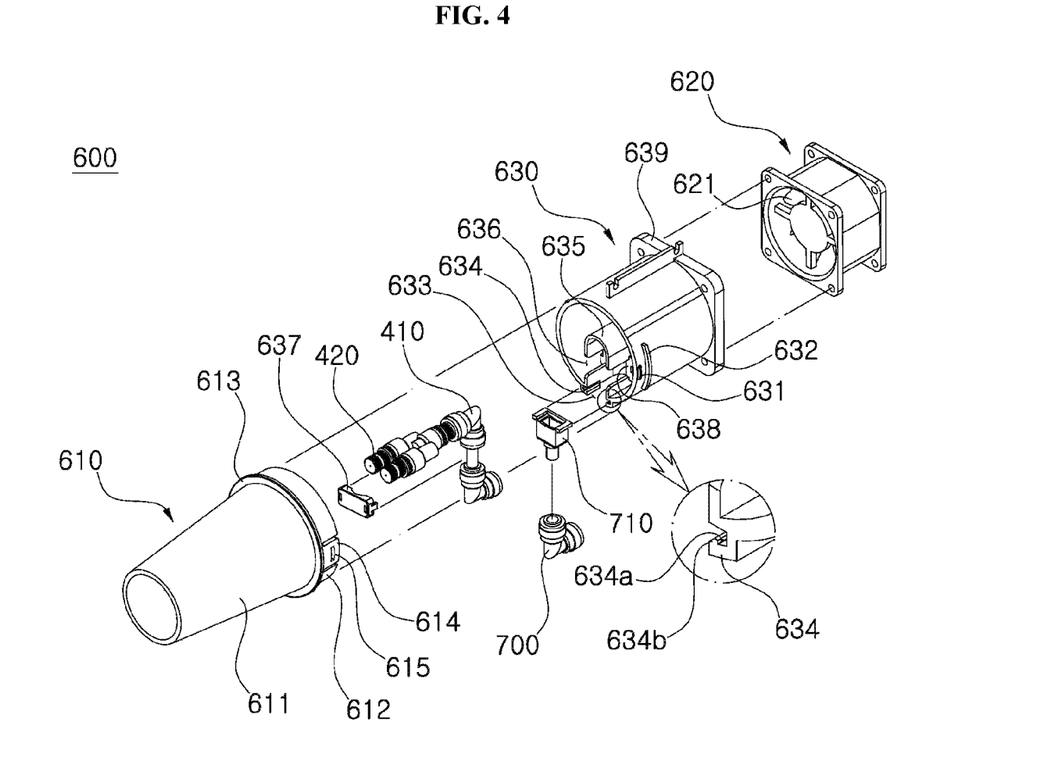
FIG. 4 is an exploded perspective view of the injection nozzle according to an embodiment of the present invention.
Figure 5:
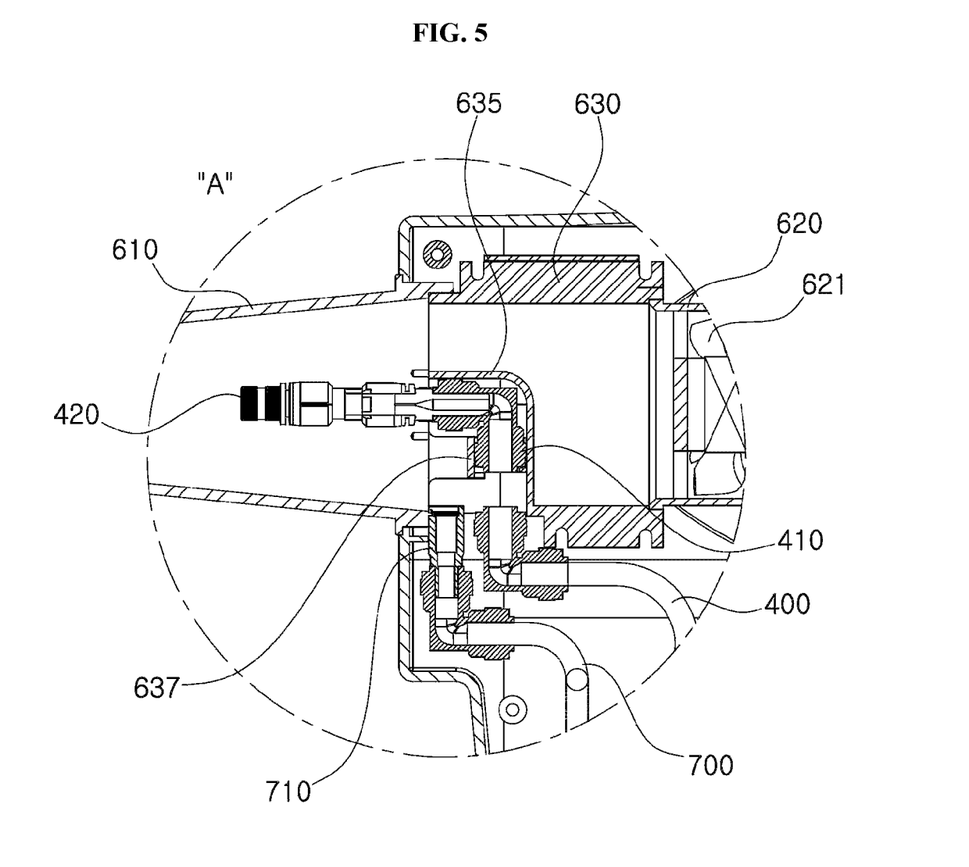
FIG. 5 is an enlarged view of part "A" of FIG. 3.

Referring to FIGS. 4 and 5, the injection nozzle 600 may be provided in front of the handle 210 and on the upper front end of the housing 200, and the chemicals supplied to the injection nozzle 600 through the chemical feed pipe 500 may be injected in a front direction.

Herein, the injection nozzle 600 may include: a nozzle member 610 in a conical form with a gradually narrower width from a rear end to a front end thereof; a blower 620 installed in the rear of the nozzle member 610 to blow air in the front direction; and a connection part 630 formed between the nozzle member 610 and the blower 620, into which an end of the chemical feed pipe 400 is inserted.

A through-hole 270 may be formed on the top of the front end of the housing 200, and the rear end of the nozzle member 610 may be coupled to the through-hole 270. The nozzle member 610 may include a conical body 611, a flange part 612 extending from the rear end of the body, and a locking part 613 having a width extending around the front end of the flange part 612.

The nozzle member 610 is coupled such that the rear end of the locking part 613 is locked around a front periphery of the through-hole 270 of the housing 200. Further, a plurality of elastic blades 614 may be cut and formed along the periphery of the flange part 612. The elastic blades 614 may be elastically supported inward and elastically bound to the front end of the connection part 630 when coupled to the connection part 630.

The connection part 630 may have a cylindrical shape, and the front end of the connection part 630 may be coupled to the rear end of the nozzle member 610. At this time, coupling protrusions 631 at both sides of the front end of the connection part 630 may be inserted and coupled to coupling grooves 615 formed in the elastic blades 614 of the nozzle member 610. Further, locking protrusions 632 may be formed to protrude at a predetermined distance in the rear of the coupling protrusions 631, and the rear end of the nozzle member 610 may be locked and supported on the locking protrusions 632.

Further, an insert hole 633 may be cut and formed on the bottom of the front end of the connection part 630 in order to insert the chemical feed pipe 400 into the hole. At both sides of the front end of the insertion hole 633, guides 634 may be protruded and formed. Further, a guide groove 634a may be formed inside the guide 634 in a longitudinal direction of the guide 634. The guide 634 is for coupling the chemical recovery pipe 700, wherein a hose bracket 710 coupled to an end of the chemical recovery pipe 700 is coupled to the guide 634. In addition, a locking jaw 634b for preventing release of the hose bracket 710 may be protruded and formed at one side of the guide groove 634a.

A 'L'-shaped connector 410 may be coupled to the end of the chemical feed pipe 400 inserted into the connection part 630 through the insertion hole 633, and a pair of branched mist nozzles 420 may be coupled to the front end of the connector 410. That is, the chemicals supplied through the chemical feed pipe 400 may be sprayed through the mist nozzles 420.

In order to prevent the mist nozzle 420 from flowing when spraying the chemicals, a connector support member 635 that surrounds and supports the connector 410 may be protruded and formed along an upper periphery of the insert hole 633. At this time, a cutout 636 may be formed in the middle of the connector support member 635, and may be coupled with a cover 637. After inserting the connector 410 into the connector support member 635, the user can couple the cover to the cutout 636 so as to prevent the flow of the connector 410 when spraying the chemical mist. At a rear end of the cutout 636, coupling plates 638 for coupling the cover 637 with the cutout may be provided to protrude at both sides of the rear end.

At the rear end of the connection part 630, a rectangular coupling flange 639 may be extended, and the blower 620 may be coupled to the rear end of the coupling flange 639. A blower fan 621 capable of rotating by driving a motor (not shown) may be mounted inside the blower 620, and operation of the blower fan 621 may be controlled according to ON/OFF of the power button 220.

With regard to the portable sterilizer 100 according to an embodiment of the present invention, a battery 230 may be equipped in a replaceable manner, and the chemicals vaporized as ultra-fine particles by the blower fan 621 may be sprayed far away in the front direction.

For example, the portable sterilizer 100 according to an embodiment of the present invention may be operated in the following order. First, when the power button 220 is turned ON, the water pump 500 begins operation along with the blower fan 621, and the chemicals stored in the chemical tank 300 may be supplied to the injection nozzle 600 along the chemical feed pipe 400 by the water pump 500.

The chemicals supplied along the chemical feed pipe 400 may be sprayed through the mist nozzle 420 and, at this time, may be sprayed forward with the wind blowing from the rear side by the blower fan 621. When spraying the mist, the chemicals smeared on an inner surface of the nozzle member 610 may flow down along the inner surface of the nozzle member 610 and then flow into the insert hole 633 of the connection part. Subsequently, the chemicals may be returned back to the chemical tank 300 through the hose bracket 710 and the chemical recovery pipe 700.

Although the embodiments of the present invention have been described above, it is understood that those of ordinary skill in the art to which the present invention pertains may make various modifications without departing from the scope of the claims of the present invention.

According to the portable sterilizer of the present invention, disinfection and disease prevention efficiencies may be improved while preventing secondary contamination.

Further, according to the portable sterilizer of the present invention, the operation can be continuously implemented with a new battery additionally charged when the previous battery is discharged.

What is claimed is:
1. A portable sterilizer, comprising:
   a housing in which a space is formed and an injection nozzle is provided at a front end of the housing;
   a chemical tank provided on one side of the space in the housing;
   a chemical feed pipe formed between the chemical tank and the injection nozzle;
   a water pump installed on one side of the chemical feed pipe to supply chemicals to the injection nozzle through the chemical feed pipe; and
   a fixing bracket for mounting and fixing the water pump on the inner surface of one side of the housing,
   wherein the fixing bracket comprises:
      a ring type body combined to surround an outer circumference of the water pump;
      a pair of support parts being spaced apart from one side of the body by a predetermined distance and extending outward, which obliquely extend such that a distance between each other increases toward the outside of the body; and
      a coupling part bent outward and extending from an end of the support part, in which a fastening hole is formed to perforate through the coupling part,
   wherein a plurality of coupling bosses are protruded from the inner surface of one side of the housing, and the fixing bracket is fixed to the inside of the housing by a fastening member which penetrate the fastening hole of the coupling part and fastened to the coupling bosses, and
   wherein a reinforcing member is provided on the outside of the coupling boss to support the coupling part of the fixing bracket.

2. The portable sterilizer according to claim 1, wherein a handle is provided on the top of a rear end of the housing.

3. The portable sterilizer according to claim 1, wherein a battery is detachably coupled to the bottom of the rear end of the housing.

4. A portable sterilizer comprising:
   a housing in which a space is formed and an injection nozzle is provided at a front end of the housing;
   a chemical tank provided on one side of the space in the housing;
   a chemical feed pipe formed between the chemical tank and the injection nozzle; and
   a water pump installed on one side of the chemical feed pipe to supply chemicals to the injection nozzle through the chemical feed pipe,
   wherein the injection nozzle includes: a conical nozzle member formed to become narrower in width from the rear end to the front end; a blower installed in the rear of the nozzle member and provided with a blower fan; and a cylindrical connection part between the nozzle member and the blower fan, into which an end of the chemical feed pipe is inserted, wherein the nozzle member comprises:
- a conical body;
- a flange part extending from the rear end of the body;
- a locking part extending in width along the periphery of the front end of the flange part; and
- a plurality of elastic blades which are cut and formed along the periphery of the flange part, elastically supported inward, and elastically bound to the connection part, wherein the connection part comprises:
- coupling protrusions which are formed to protrude at both sides of the front end of the connection part, and are inserted and coupled to coupling grooves in the elastic blades;
- locking protrusions which are formed to protrude at a predetermined distance in the rear of the coupling protrusions, and on which the rear end of the nozzle member is locked and supported;
- an insert hole cut and formed on the bottom of the front end of the connection part in order to insert the chemical feed pipe into the hole;
- guides formed to protrude at both sides of the front end of the insertion hole;
- a guide groove formed inside the guide in a longitudinal direction of the guide; and
- a locking jaw formed to protrude at one side of the guide groove.

5. The portable sterilizer according to claim 4, wherein a L-shaped connector is coupled to an end of the chemical feed pipe, and a pair of mist nozzles is coupled to the front end of the connector.

6. The portable sterilizer according to claim 4, further comprising a chemical recovery pipe that extends from the connection part to the chemical tank so as to return the chemicals remaining in the injection nozzle back to the chemical tank,
wherein a hose bracket coupled to an end of the chemical recovery pipe is coupled to the guide, and release of the hose bracket is prevented by the locking jaw.

* * * * *